United States Patent
Ly et al.

(10) Patent No.: US 12,099,012 B2
(45) Date of Patent: Sep. 24, 2024

(54) REMOTE MICROSCOPY FOR BIOLOGICAL SCIENCES

(71) Applicant: The Regents of the University of California, Oakland, CA (US)

(72) Inventors: Victoria Ly, Santa Cruz, CA (US); Pierre Baudin, Santa Cruz, CA (US); Pattawong Pansodtee, Santa Cruz, CA (US); Erik Jung, Santa Cruz, CA (US); Robert Currie, Santa Cruz, CA (US); David Haussler, Santa Cruz, CA (US); Mircea Teodorescu, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 107 days.

(21) Appl. No.: 17/738,251

(22) Filed: May 6, 2022

(65) Prior Publication Data

US 2022/0360703 A1 Nov. 10, 2022

Related U.S. Application Data

(60) Provisional application No. 63/242,449, filed on Sep. 9, 2021, provisional application No. 63/184,915, filed (Continued)

(51) Int. Cl.
*G06T 7/00* (2017.01)
*C12M 1/12* (2006.01)
(Continued)

(52) U.S. Cl.
CPC ......... *G01N 21/6458* (2013.01); *C12M 25/06* (2013.01); *G01N 21/6486* (2013.01);
(Continued)

(58) Field of Classification Search
CPC .......... G01N 21/6458; G01N 21/6486; G01N 2201/021; G01N 2201/062; C12M 25/06;
(Continued)

(56) References Cited

U.S. PATENT DOCUMENTS 9,134,524 B2 * 9/2015 Yamamoto ........... G02B 21/367
10,372,967 B1 * 8/2019 Vácha ..................... G06T 7/194
(Continued)

OTHER PUBLICATIONS

Zhao, H., et al., "A screening platform for glioma growth and invasion using bioluminescence imaging", J. neurosurgery 111, 238-246 (2009).
(Continued)

*Primary Examiner* — Frank F Huang
(74) *Attorney, Agent, or Firm* — Carter, DeLuca & Farrell LLP

(57) ABSTRACT

An imaging system includes an imaging device having a holder configured to hold a cell culture plate with a plurality of wells. The imaging device also includes an imaging assembly having a plurality of imaging units, each of which is configured to image one well of the plurality of wells. The imaging system also includes a storage platform in communication with the imaging device configured to receive a plurality of images from the imaging device. The system further includes a computer in communication with the imaging device and the storage platform. The computer is configured to control the imaging device and to display at least one image of the plurality of images.

19 Claims, 13 Drawing Sheets

Related U.S. Application Data on May 6, 2021, provisional application No. 63/184,913, filed on May 6, 2021.

(51) Int. Cl.
| | |
|---|---|
| G01N 21/64 | (2006.01) |
| G02B 21/36 | (2006.01) |
| G06T 7/571 | (2017.01) |
| H04N 5/265 | (2006.01) |
| H04N 23/62 | (2023.01) |
| H04N 23/66 | (2023.01) |
| H04N 23/90 | (2023.01) |

(52) U.S. Cl.
CPC ............ *G02B 21/365* (2013.01); *G06T 7/571* (2017.01); *H04N 5/265* (2013.01); *H04N 23/62* (2023.01); *H04N 23/66* (2023.01); *H04N 23/90* (2023.01); *G01N 2201/021* (2013.01); *G01N 2201/062* (2013.01); *G06T 2207/10056* (2013.01); *G06T 2207/10148* (2013.01); *G06T 2207/30024* (2013.01); *G06T 2207/30072* (2013.01)

(58) Field of Classification Search
CPC ...... C12M 41/36; G02B 21/365; G02B 21/26; G06T 7/571; G06T 2207/10056; G06T 2207/10148; G06T 2207/30024; G06T 2207/30072; H04N 5/265; H04N 23/62; H04N 23/66; H04N 23/90; H04N 23/60; H04N 23/676; H04N 23/50; H01L 27/14601; H01L 27/14634; H01L 27/14636

See application file for complete search history.

(56) References Cited

U.S. PATENT DOCUMENTS

| | | | | |
|---|---|---|---|---|
| 10,754,140 | B2* | 8/2020 | Chan ...................... | G02B 21/02 |
| 2015/0049919 | A1* | 2/2015 | Humal ................... | A01K 47/06 382/110 |
| 2015/0297620 | A1* | 10/2015 | Boletta ................ | A61K 31/436 514/23 |
| 2016/0187199 | A1* | 6/2016 | Brunk ................... | G01J 3/0208 348/89 |
| 2017/0161545 | A1* | 6/2017 | Champlin ............ | G06V 20/695 |
| 2018/0008982 | A1* | 1/2018 | Ying ...................... | C12M 47/04 |
| 2022/0318575 | A1* | 10/2022 | Linzbach .......... | G06F 18/24143 |

OTHER PUBLICATIONS

Specht, E. A., et al., "A critical and comparative review of fluorescent tools for live-cell imaging", Annu. review physiology 79, 93-117 (2017).
Godin, A. G., et al., "Super-resolution microscopy approaches for live cell imaging", Biophys. Journal 107, 1777-1784 (2014).
Miller, A. R. et al., "Portable, battery-operated, low-cost, bright field and fluorescence microscope", PloS one 5, e11890 (2010).
Selinummi, J. et al., "Bright field microscopy as an alternative to whole cell fluorescence in automated analysis of macrophage images", PloS one 4, e7497 (2009).
Hernández Vera, R., et al., "A modular and affordable time-lapse imaging and incubation system based on 3d-printed parts, a smartphone, and off-the-shelf electronics", PLoS One 11, e0167583 (2016).
Savas, J., et al., "Toward fully three-dimensional-printed miniaturized confocal imager", Opt. Eng. 57, 041402 (2018).
Wincott, M. B. et al. "Democratising" microscopi": a 3d printed automated XYZT fluorescence imaging system for teaching, outreach and fieldwork", bioRxiv (2020).
Yao, S., et al., "Automatic three-dimensional imaging for blastomere identification in early-stage embryos based on brightfield microscopy", Opt. Lasers Eng. 130, 106093 (2020).
Zamxaka, M., et al., "Microbiological and physico-chemical assessment of the quality of domestic water sources in selected rural communities of the eastern cape province, south africa", Water Sa 30, 333-340 (2004).
Ferreira, L. M. et al. "Effective participatory science education in a diverse latin american population", Palgrave Commun. 5, 63 (2019).
Giacomotto, J. & Ségalat, L. "High-throughput screening and small animal models, where are we?", Br. journal pharmacology 160, 204-216 (2010).
Willis, S., "The maker revolution", Computer 51, 62-65 (2018).
Barber, K. & Mostajo-Radji, "M. A. Youth networks' advances toward the sustainable development goals during the covid-19 pandemic", Front. Sociol. 5: 589539. doi: 10.3389/fsoc (2020).
Coakley, M. F. et al., "The nih 3d print exchange: a public resource for bioscientific and biomedical 3d prints", 3D printing additive manufacturing 1, 137-140 (2014).
Ambrose, B. et al., "Democratizing single-molecule fret: An open-source microscope for measuring precise distances and biomolecular dynamics", Biophys. J. 118, 614a (2020).
Gross, B. C., et al., "Evaluation of 3d printing and its potential impact on biotechnology and the chemical sciences", ACS Publ. (2014).
Baden, T. et al., "Open labware: 3-d printing your own lab equipment", PLoS biology 13, e1002086 (2015).
Alessandri, K. et al., "All-in-one 3d printed microscopy chamber for multidimensional imaging, the universlide", Sci. reports 7, 1-10 (2017).
Ventola, C. L., "Medical applications for 3d printing: current and projected uses", Pharm. Ther. 39, 704 (2014).
Beattie, R. J., et al., "Sparking curiosity through open-source platforms in education and science. Front", Educ. 5, 8 (2020).
Brown, J. W. et al., "Single-molecule detection on a portable 3d-printed microscope", Nat. communications 10, 1-7 (2019).
Khan, A., et al., "A low-cost 3d printed microfluidic bioreactor and imaging chamber for live-organoid imaging", Biomicrofluidics (2021).
Chagas, A. M., et al., "TheC 100 lab: A 3d-printable open-source platform for fluorescence microscopy, optogenetics, and accurate temperature control during behaviour of zebrafish, *Drosophila*, and caenorhabditis elegans", PLoS biology 15, e2002702 (2017).
Kim, S. B. et al., "A mini-microscope for in situ monitoring of cells", Lab on a Chip 12, 3976-3982 (2012).
Diederich, B. et al., "A versatile and customizable low-cost 3d-printed open standard for microscopic imaging", Nat. communications 11, 1-9 (2020).
Wang, Z. et al., "A high-resolution minimicroscope system for wireless real-time monitoring", IEEE Transactions on Biomed. Eng. 65, 1524-1531 (2017).
Zhang, Y. S. et al., "A cost-effective fluorescence mini-microscope for biomedical applications", Lab on a Chip 15, 3661-3669 (2015).
Zhang, C., et al., "Open-source 3d-printable optics equipment", PloS one 8, e59840 (2013).
Collins, J. T. et al., "Robotic microscopy for everyone: the openflexure microscope", Biomed. Opt. Express 11, 2447-2460 (2020).
Cybulski, J. S., et al., "Foldscope: origami-based paper microscope", PloS one 9, e98781 (2014).
Kim, H. et al., "Ludusscope: accessible interactive smartphone microscopy for life-science education", PloS one 11, e0162602 (2016).
Aidukas, T., et al., "Low-cost, sub-micron resolution, wide-field computational microscopy using opensource hardware", Sci. reports 9, 1-12 (2019).
Bohm, A., "An inexpensive system for imaging the contents of multi-well plates", Acta Crystallogr. Sect. F: Struct. Biol. Commun. 74, 797-802 (2018).
Merces, G. O. et al., "The incubot: A 3d printer-based microscope for long-term live cell imaging within a tissue culture Incubator", BioRxiv (2020).
Gürkan, G.& Gürkan, K., "Incu-stream 1.0: an open-hardware live-cell imaging system based on inverted bright-field microscopy

(56) References Cited

OTHER PUBLICATIONS and automated mechanical scanning for real-time and long-term imaging of microplates in incubator", IEEE Access 7, 58764-58779 (2019).
Kim, J., Henley,et al., "Incubator embedded cell culture imaging system (emsight) based on fourier ptychographic microscopy", Biomed. optics express 7, 3097-3110 (2016).
Uno, A. Arduino uno. online, (https://store. arduino. cc/usa/arduino-uno-rev3, diakses) 4 (2019).
Pi, R. Raspberry pi 4. online.(https://www. raspberrypi. org) (2015).
Beam, M. Makerbeam 10mm×10mm. online].(https://www.makerbeam.com/makerbeam/ (2021).
Fruit, A. Zero spy camera for raspberry pi zero. online.(https://www.adafruit.com/product/3508) (2015).
Goda, T. et al., "Genetic screens for mutations affecting development of xenopus tropicalis", PLoS Genet. 2, e91 (2006).
Borodinsky, L. N., "Xenopus laevis as a model organism for the study of spinal cord formation, development, function and regeneration", Front. neural circuits 11, 90 (2017).
Olmstead, A. W. et al., "Reproductive maturation of the tropical clawed frog: Xenopus tropicalis", Gen. comparative endocrinology 160, 117-123 (2009).
Hirsch, N., et al., "Xenopus, the next generation: X. tropicalis genetics and genomics", Dev. dynamics: an official publication Am. Assoc. Anat. 225, 422-433 (2002).
Mcnamara, S., et al., "Husbandry, general care, and transportation of xenopus laevis and xenopus tropicalis", Methods Mol Biol., 1-17 (Springer, 2018).
Khokha, M. K. et al., "Techniques and probes for the study of xenopus tropicalis development", Dev. dynamics: an official publication Am. Assoc. Anat. 225, 499-510 (2002).
Keller, R. & Sutherland, A., "Convergent extension in the amphibian, xenopus laevis", In Current topics in developmental biology, vol. 136, 271-317 (Elsevier, 2020).
Baldwin, A., Kim, J. & Wallingford, J. B., "Global analysis of cell behavior and protein localization dynamics reveals region-specific functions for shroom3 and n-cadherin during neural tube closure", bioRxiv (2021).
Huebner, R. J. et al., "Cadherin clustering controls heterogeneous, asymmetric junction dynamics during vertebrate axis elongation", bioRxiv (2020).
Abe-Fukasawa, N., et al., "Novel 3d liquid cell culture method for anchorageindependent cell growth, cell imaging and automated drug screening", Sci. reports 8, 1-12 (2018).
Almassalha, L. M. et al., "Label-free imaging of the native, living cellular nanoarchitecture using partial-wave spectroscopic microscopy", Proc. Natl. Acad. Sci. 113, E6372-E6381 (2016).
Martin, H. L. et al., "High-content, high-throughput screening for the identification of cytotoxic compounds based on cell morphology and cell proliferation markers", PloS one 9, e88338 (2014).
Dempsey, G. T. et al., "Cardiotoxicity screening with simultaneous optogenetic pacing, voltage imaging and calcium imaging", J. pharmacological toxicological methods 81, 240-250 (2016).
Honarnejad, K. et al., "Fret-based calcium imaging: a tool for high-throughput/content phenotypic drug screening in alzheimer disease", J. biomolecular screening 18, 1309-1320 (2013).
Park, J., et al., "Estimates of particulate matter inhalation doses during three-dimensional printing: How many particles can penetrate into our body?", Indoor air (2020).
Pearce, J. M., "Building research equipment with free, open-source hardware", Science 337, 1303-1304 (2012).
Mendoza-Gallegos, et al., "An affordable and portable thermocycler for real-time pcr made of 3d-printed parts and off-the-shelf electronics", Anal. chemistry 90, 5563-5568 (2018).
Kwon, H.-S. et al., "Performance of minipcr tm mini8, a portable thermal cycler", Anal. Sci. Technol. 29, 79-84 (2016).
Byagathvalli, G., et al., "A 3d-printed hand-powered centrifuge for molecular biology", PLoS biology 17, e3000251 (2019).
González-González, E., et al., "Portable and accurate diagnostics for covid-19: Combined use of the minipcr thermocycler and a well-plate reader for sars-cov-2 virus detection", PloS one 15, e0237418 (2020).
Boguraev, A.-S. et al., Successful amplification of dna aboard the international space station:, NPJ microgravity 3, 1-4 (2017).
Hossain, Z. et al., "Interactive and scalable biology cloud experimentation for scientific inquiry and education", Nat. biotechnology 34, 1293-1298 (2016).
Klimaj, S. D., et al., "A high-throughput imaging and quantification pipeline for the evos imaging platform", Plos one 15, e0236397 (2020).
Ruckdäschel, S., "Time lapse imaging of spheroids-zencellowl incubator microscope", OMNI Life Sci. (2017).
Early, J. J. et al., "An automated high-resolution in vivo screen in zebrafish to identify chemical regulators of myelination", Elife 7, e35136 (2018).
Tsuji, N. et al., "Whole organism high content screening identifies stimulators of pancreatic beta-cell proliferation", PloS one 9, e104112 (2014).
Lemieux, G. A. et al., A whole-organism screen identifies new regulators of fat storage, Nat. chemical biology 7, 206-213 (2011).
Schreiber, K., et al., "A high-throughput chemical screen for resistance to pseudomonas syringae in *Arabidopsis*", The Plant J. 54, 522-531 (2008).
Renner, H. et al., "A fully automated high-throughput workflow for 3d-based chemical screening in human midbrain organoids", Elife 9, e52904 (2020).
Schuster, B. et al., "Automated microfluidic platform for dynamic and combinatorial drug screening of tumor organoids", Nat. communications 11, 1-12 (2020).
Willsey, H. R. et al., "The neurodevelopmental disorder risk gene dyrk1a is required for ciliogenesis and control of brain size in xenopus embryos", Development 147 (2020).
Nieuwkoop, P. D. & Faber, J., "Normal table of xenopus laevis (daudin)", Copeia 1958, 65-65 (1958).
Thomson, J. A. et al., "Embryonic stem cell lines derived from human blastocysts", science 282, 1145-1147 (1998).

* cited by examiner

REMOTE MICROSCOPY FOR BIOLOGICAL SCIENCES

CROSS-REFERENCE TO RELATED APPLICATION

The present application claims the benefit of and priority to U.S. Provisional Application No. 63/184,913, filed on May 6, 2021; U.S. Provisional Application No. 63/184,915, filed on May 6, 2021; and U.S. Provisional Application No. 63/242,449, filed on Sep. 9, 2021. The entire disclosures of each of the foregoing applications are incorporated by reference herein.

GOVERNMENT LICENSE RIGHTS

This invention was made with government support under the National Institute of Mental Health of the National Institutes of Health under Award No. R01MH120295, the National Science Foundation under Award No. NSF 2034037, and the National Human Genome Research Institute under Grant No. T32HG008345. The Government has certain rights in the invention.

BACKGROUND

Laboratory facilities may be difficult to access in person. Pandemics, natural disasters, injury, or illness can all make physical access impossible or impractical. Remote management and automated operation can have a considerable effect on the quality and quantity of work performed at a laboratory. In addition, biological science has been experiencing a crisis of reproducibility. Scientists and technicians following prescribed protocols are often unable to replicate each other's results. The use of automation in laboratory experiments might help address this issue.

SUMMARY

Techniques for remote operation of laboratory equipment are available at varying levels of cost and complexity. Further development of low-cost solutions for remote laboratory control provides options for institutions with limited resources. Cost savings may be result from incorporating innovations from the Internet of Thing (IoT) space into low-cost networked devices.

Remote laboratory environments can also be used in educational settings alongside fully simulated virtual labs. Virtual laboratories may be used as a replacement or a supplement to traditional laboratory work. Virtual laboratories also expose new users and students to the concept of the scientific process through simulation of an experiment. Remote laboratories allow users to manipulate real laboratory equipment without in-person access to the lab. Remote microscopy is one aspect of many remote laboratory experiments. In particular, remote microscopy allows users to remotely manipulate biological samples such as whole organisms, organoids, embryos, cells, and microorganisms in real time and view the results through a camera.

The imaging device according to the present disclosure provides simultaneous multi-well imaging and may perform longitudinal brightfield z-stack imaging of any suitable cell culture plate, including conventional 24-well cell culture plates. The imaging device is also configured to capture 3D z-stack image data—stacks of images and/or video at different focal layers, which is referred to as "z-plane stack" or "z-stack" due to the focal planes being stacked along a vertical, or z-axis. The imaging device is also configured to simultaneously images in each one of a plurality (e.g., 24) of wells at multiple focal planes at any suitable frequency which may be impractical to perform manually. The imaging frequency may be from about 1 minute to about 24 hours, and images may be taken for any suitable period of time, which may be from 1 hour to about 30 weeks. The resolution and imaging frequency of the z stack may be modified remotely.

The imaging device is designed to illuminate the samples using one or more lighting sources from above and/or below the cell culture plate. Diffused illumination from below results in images that show contours and surface features. Illumination from above results in more visible detail and can show internal structures if the sample is sufficiently translucent. The flexibility of using different illumination techniques emulates commercial brightfield microscopes. The imaging device also includes an alignment platform that supports a cell culture plate holding biological samples during an experiment. The alignment platform may be moved along two axes (e.g., x axis and y axis) defining a horizontal plane.

The imaging device further includes a plurality of imaging units, which may correspond to the number of wells of the cell culture plate, e.g., 24. The imaging units are coupled to an elevator platform configured to along one or more support columns. One or more stepper motors are configured to move the elevator platform vertically along a vertical axis (e.g., z axis) transverse to the horizontal plane of the alignment platform. The stepper motors may have a travel per step rate of from about 1 µm to about 10 µm to allow for focusing of specific biological features and collecting z-stack imaging. The imaging device may be controlled remotely via a remote computer, allowing for automatic imaging with minimal intervention from the investigator. Images are uploaded to the remote computer or server as they are captured allowing the user to view the results in near real time.

The present disclosure also provides a data pipeline to facilitate remote operation and to control communication between various modules of the imaging device. A web-based interface may be used to set parameters for imaging experiments and to view results in near real-time remotely, e.g., via Internet. This capability allows for high throughput parallel remote microscopy at an affordable price point to many sectors that could not previously access such systems. The three-dimensional stack data (i.e., multiple pictures taken at different focal lengths along a vertical axis) captured by the imaging device allows for imaging of two-dimensional or three-dimensional samples.

Examples of using the imaging device according to the present disclosure are also provided and include longitudinal imaging of whole organisms to longitudinally track different animal models of development and regeneration, including *Xenopus tropicalis* (frogs) embryos, *Danio rerio* (zebrafish), and neural spheroids. The data pipeline is capable of feeding these z-stacks into software that generates extended depth of field (EDoF) composite images to simplify the end user's visual analysis of longitudinal changes in a three-dimensional sample.

According to one aspect of the present disclosure, an imaging system is disclosed. The imaging system includes an imaging device having a holder configured to hold a cell culture plate with a plurality of wells. The imaging device also includes an imaging assembly having a plurality of imaging units, each of which is configured to image one well of the plurality of wells. The imaging system also includes a storage platform in communication with the imaging device. The storage platform is configured to receive a plurality of images from the imaging device. The system further includes a computer in communication with the imaging device and the storage platform. The computer is configured to control the imaging device and to display at least one image of the plurality of images.

Implementations of the above embodiment may include one or more of the following features. According to one aspect of the above embodiment, the imaging system may further include an image processing platform configured to generate a time lapse video from the plurality of images and/or an extended depth of field composite image from the plurality of images. Each of the imaging units may be configured to capture a plurality of images of a corresponding well over a period of time. Each of the imaging units may be configured to capture a plurality of images of a corresponding well at a plurality of focal planes. The imaging assembly is movable relative to the cell culture plate such that each of the imaging units may be configured to capture an image at each focal plane of the plurality of focal planes. The computer may further include a control console configured to receive one or more parameters as user input and to transmit the parameter(s) to the imaging device. The imaging device may further include a hub controller and a plurality of camera controllers, each of which is coupled to one imaging unit of the plurality of imaging units. The hub controller may be further configured to query each of the camera controllers in a sequential manner. Each of the camera controllers may be configured to transmit at least one image as a response to a query from the hub controller. The hub controller may be further configured to check whether the response from each of the camera controllers has timed out.

According to another aspect of the present disclosure, a method for imaging a cell culture plate using an imaging device is disclosed. The method includes receiving one or more parameter(s) at an imaging device, which includes: a holder configured to hold a cell culture plate having a plurality of wells and an imaging assembly having a plurality of imaging units, each of which may be configured to image one well of the plurality of wells. The method also includes operating the imaging device based on the parameter(s) to capture one or more image(s) of at least one well and transmitting the image(s) to a storage platform.

Implementations of the above embodiment may include one or more of the following features. According to one aspect of the above embodiment, the parameter may be a number of focal planes. The method may further include moving the imaging assembly relative to the holder along a vertical axis transverse to a plane defined by the holder and stopping the imaging assembly at each of the focal planes. The method may further include operating the imaging assembly to capture an image at each of the focal planes. The method may further include generating an extended depth of field composite image from the images taken at each of the focal planes.

The parameter may be a number of imaging sequences over a time period. The method may further include operating the imaging assembly for a set number of imaging sequences during the time period. The method may further include generating a time lapse video from images taken during the imaging sequence. The method may further include inputting the parameter at a control console having a graphical user interface. The method may further include displaying the at least one image on an image viewer of the control console. The parameter(s) may be a number of images in a stack, a distance between focal planes, initial offset distance, a duration of experiment, or a time between imaging sequences.

BRIEF DESCRIPTION OF DRAWINGS

Various embodiments of the present disclosure are described herein below with reference to the figures wherein.

DETAILED DESCRIPTION

The present disclosure provides for an imaging device having a plurality of cameras disposed on a movable platform. The cameras are suitable for imaging individual wells of a cell culture plate. The distance of the cameras relative to the culture plate is adjustable by using one or more of the motors to raise or lower the cameras to focus on different focal planes of the samples in the wells of the cell culture plate. The imaging device is configured to capture stacks of images and/or video at different focal planes (also referred to as "focal layers"). Such stacks are referred to as "z-plane stacks" or "z-stacks" due to the focal planes being stacked along a vertical, or z, axis. Z-stack data provides depth information and ensures that all visible features of the sample are captured.

Figure 1:
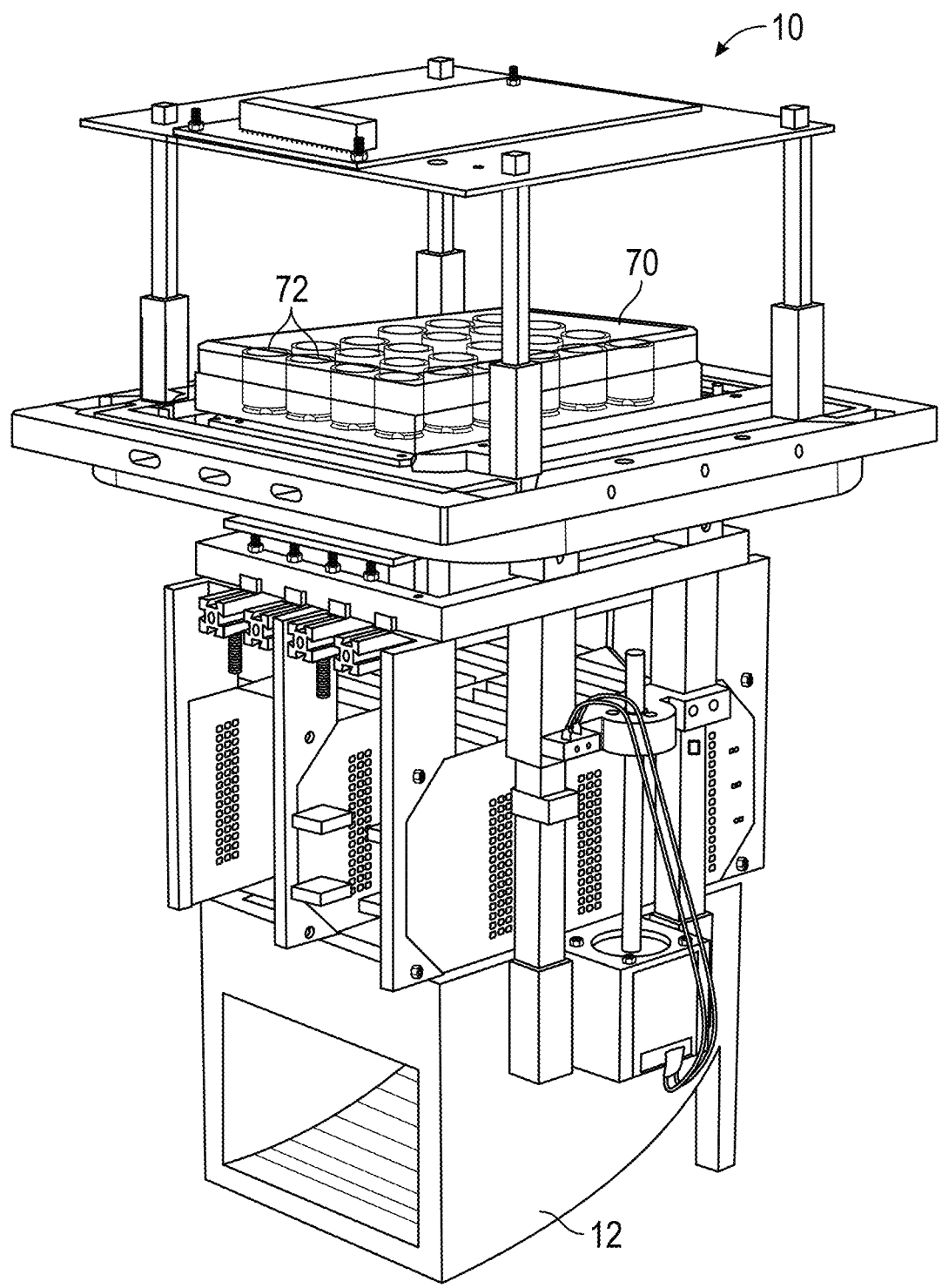
FIG. 1 is an imaging device holding a cell culture plate according to one embodiment of the present disclosure.
Figure 2:
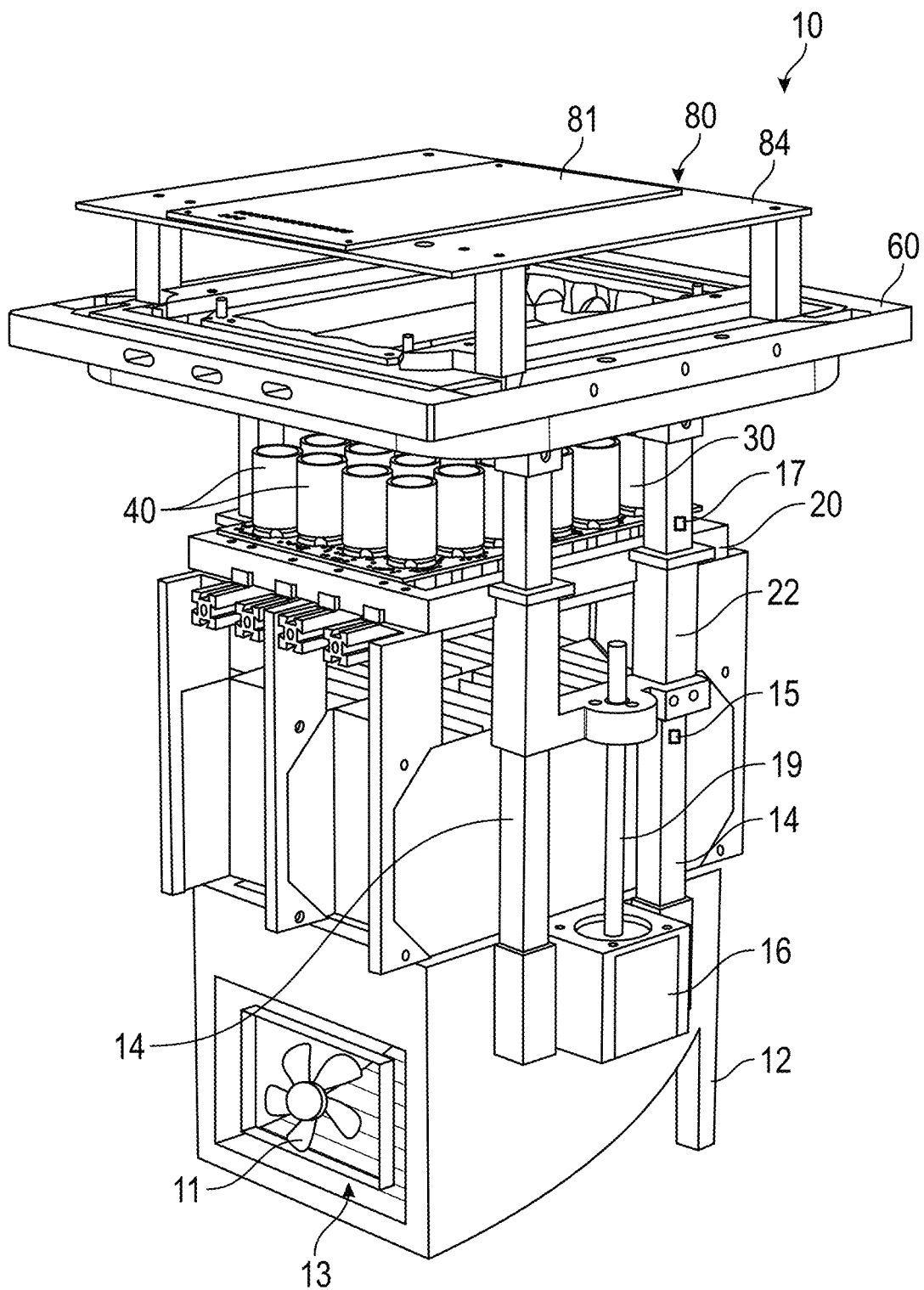
FIG. 2 is a perspective view of the imaging device FIG. 1.

FIGS. 1 and 2 show an imaging device 10 having a base 12 with one or more columns 14 extending vertically from the base 12. The base 12 may include an intake 13 and a fan 11 disposed in communication with the intake 13 for heat dissipation. The base 12 and/or the footprint of the imaging device 10 may be from about 100 cm$^2$ to about 500 cm$^2$ providing for portability of the imaging device 10. In embodiments, the imaging device 10 may have a width and depth of from about 30 cm to about 70 cm and may have a height from about 30 cm to about 80 cm.

The columns 14 may be formed from any suitable rigid material, such as metal. The columns 14 may be formed from aluminum extrusions, such as those available from MakerBeam of Utrecht, Netherlands. The columns 14 may have a square cross-section (e.g., 10 mm×10 mm) and have a length of about 200 mm. The columns 14 are used as guides for an elevator platform 20, which is movable vertically along the columns 14 by one or more actuators 16. The actuators 16 may be stepper motors configured to move and hold any discrete position for precisely moving the elevator platform 20. The discrete position, i.e., distance traveled per step, may be from about from about 1 μm to about 10 μm. The elevator platform 20 includes a plurality of sleeves 22, each of which is configured to slidably fit around each of columns 14. Each of the actuators 16 includes a drive shaft 19, which when actuated, moves the elevator platform 20 along a vertical axis. Various mechanical interfaces that convert rotational motion output by the actuators 16 and/or the drive shaft 19 into linear motion of the elevator platform 20 may be used, and include, but are not limited to, worm gears, bevel gears, and the like. Mechanical interfaces may be disposed at the elevator platform 20 and/or the actuators 16.

The elevator platform 20 supports an imaging assembly 30 having a plurality of imaging units 40 disposed in a matrix, i.e., a plurality of imaging arrays of imaging units 40. Each imaging array may have any suitable number of imaging units 40, which may be from 1 to 10, depending on the number of cells being imaged.

Each of the imaging units 40 includes a camera body 42 housing a camera 44 and a lens assembly 46. The camera 44 may be any digital image capturing device, such as Raspberry Pi Camera Module v2, and may have any suitable resolution, e.g., 5MP and pixel pitch of about 1.4 μm×1.4 μm. The lens assembly 46 may have an optical format of 1/2.5" and a focal length of 16 mm, such as Arducam 1/2.5" M12 mount 16 mm focal length camera lens. The lens assembly 46 may have any number of lenses and may have any desired focal length for imaging the samples "S".

Figure 3:
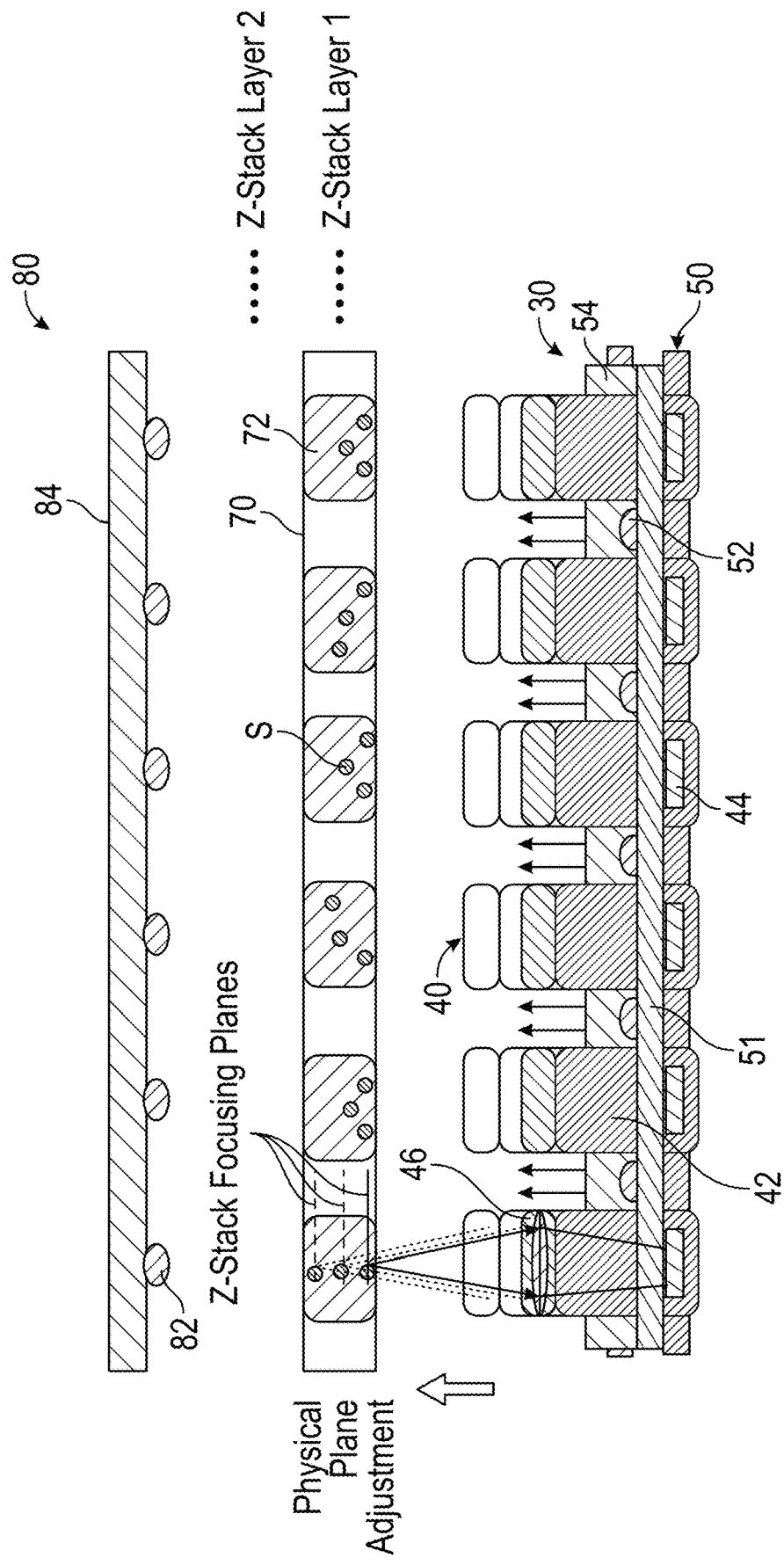
FIG. 3 is a schematic diagram of an array of imaging assemblies and the cell culture plate according to one embodiment of the present disclosure.

With reference to FIG. 3, the imaging assembly 30 also includes a first illumination assembly 50 having a substrate 51, which may be a printed circuit board (PCB) or any other suitable rigid substrate. The PCB may be a 1.6 mm FR4 two-layer PCB. The first illumination assembly 50 includes a plurality of light emitting devices 52, which may be light emitting diodes (LEDs) or the like. The LEDs 52 are disposed on the substrate 51 and are located between the imaging units 40 allowing for forward lighting of the samples "S". The first illumination assembly 50 also includes a light diffusing layer 54, which may be formed from any suitable transparent material, such as acrylics, and the like. The light diffusing layer 54 may be used to encase the LEDs 52 on the substrate 51. The light diffusing layer 54 may be machined from a sheet of acrylic, which may have a thickness from about 5 mm to about 10 mm, using CNC machines, such as Nomad883 Pro.

With reference to FIGS. 1 and 2, the imaging device 10 also includes an alignment platform 60, which is securely coupled to the columns 14. The alignment platform 60 is configured to support a cell culture plate 70 having a plurality of wells 72. The alignment platform 60 acts as an alignment platform for the cell culture plate 70 relative to the imaging assembly 30. The alignment platform 60 is disposed above the elevator platform 20 such that the imaging assembly 30 is configured to illuminate and image the samples "S" held in the wells 72 of the cell culture plate 70.

Structural components of the imaging device 10 may be formed using any additive techniques, such as 3D printing using MK3S Prusa 3D printer (PRUSA) or any other suitable 3D printer. Polylactic acid (PLA) such as Prusa Slic3r (PRUSA) or any other suitable polymers may be used. In embodiments, other 3D printable materials may be used, such as metals. The parts may be created with computer aided design (CAD) using any suitable application, such as Fusion 360 and AutoCAD (Autodesk). In embodiments, the base 12, the elevator platform 20, the alignment platform 60, and other structural components may be formed using 3D printers. The components may be printed using infill settings from about 80% to about 100% with resolution of about 0.15 mm or higher. In embodiments, supports may be used during printing.

As shown in the figure, the cell culture plate (also known as a "tissue culture plate") 70 includes 24 wells 72. In embodiments, the cell culture plate 70 may have any number of wells 72, which may be from 1 to 96 wells, including 1, 2, 4, 8, 24, 48, or 96 wells. The cell culture plate 70 may have any suitable dimensions, including width, length, and height. The wells 72 may also be of any desired dimension, e.g., diameter, depth, and spacing between neighboring wells 72. The design of the imaging device 10 is based on the type of the cell culture plate 70 being used since the number of the imaging units 40, spacing between the imaging units 40, and configuration of the imaging assembly 30 depends on the number, spacing, and configuration of the cell culture plate 70. Thus, in an exemplary embodiment where the cell culture plate 70 includes 24 wells 72, the imaging units 40 are arranged in the same configuration, i.e., in a 4×6 matrix (e.g., 4 rows and 6 columns), such that each of the wells 72 is individually imaged by a corresponding imaging unit 40.

With reference to FIGS. 2 and 3, the imaging device 10 further includes a second illumination assembly 80 disposed above the alignment platform 60. The second illumination assembly 80 is securely coupled to the alignment platform 60. The second illumination assembly 80 is configured to provide backlighting of the samples "S" held in the wells 72 of the cell culture plate 70 and allowing for brightfield imaging. The second illumination assembly 80 may include a substrate 81 (FIG. 2), which may be a PCB or any other suitable rigid substrate. The second illumination assembly 80 includes a plurality of LEDs 82, which may be light emitting diodes or the like. The LEDs 82 are disposed on the substrate 81 in the same pattern as the imaging units 40 such that each of the LEDs 82, the wells 72, and the imaging units 40 are vertically aligned, i.e., arranged along the same vertical axis. The second illumination assembly 80 also includes a light diffusing layer 84, which may be formed from any suitable transparent material, such as acrylics, and the like. The light diffusing layer 84 may be used to encase the LEDs 82 on the substrate 81.

In embodiments, the LEDs 52 and 82 may be output light at any desired wavelength and spectrum. The LEDs 52 and 82 may output white broad-spectrum light. The LEDs 52 and

82 may be MEIHUA white LEDs with a brightness of from about 228 MCD to about 450 MCD, and the brightness can be adjusted through a potentiometer. The LEDs 52 and 82 may also be NCD063W3 Chip Light Emitting Diodes.

The LEDs 52 and 82 may be defined spectrum LEDs configured to output infrared or ultraviolet light to enable fluorescent imaging of samples "S". Such light sources may be used to perform longitudinal studies of the appearance and fate of defined sub populations of cells in a complex culture having genetically encoded fluorescent reporter proteins.

Imaging of the samples "S" held within the wells 72 of the cell culture plate 70 occurs by initially adjusting each of the wells 72 to be in alignment with each of the imaging units 40, i.e., along x and y axis. In addition, the vertical distance of the elevator platform 20 is also adjusted, i.e., along z axis, to focus on a desired z-axis focal plane. This is particularly useful in samples "S" having one or more objects (e.g., embryos) disposed in different vertical (i.e., focal) planes. Transition between different focal planes is accomplished by adjusting the actuators 16 to move the elevator platform 20 by precise amounts, which may be from about 0.1 mm to about 1 mm.

Figure 4:
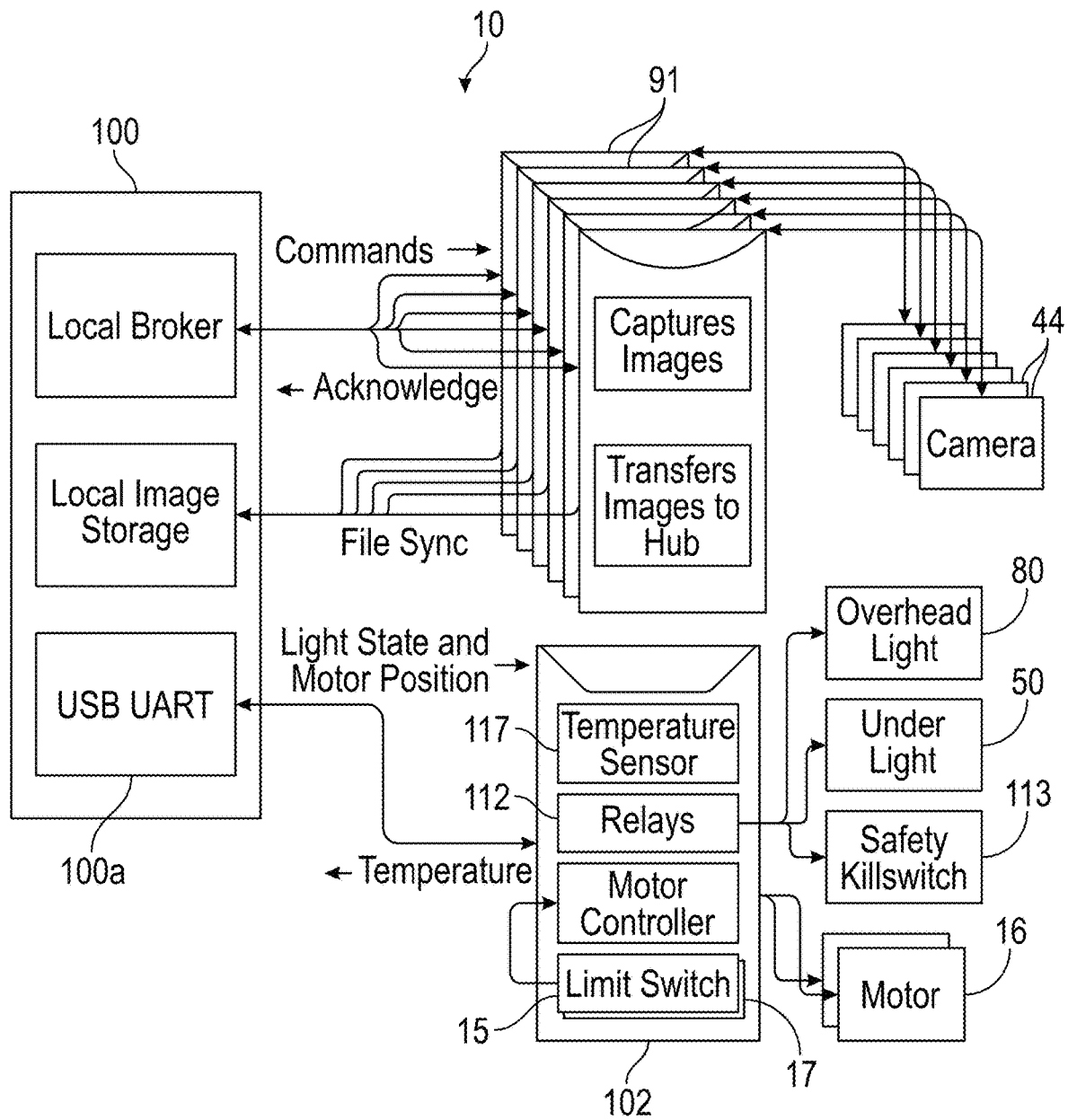
FIG. 4 is a schematic diagram of a computer architecture of the imaging device according to one embodiment of the present disclosure.

With reference to FIG. 4, the imaging device 10 includes a plurality of camera controllers 91, each of which is coupled to one of the cameras 44 using a ribbon cable or any other suitable connector. The camera controllers 91 may be any suitable computing device, such as Raspberry Pi Zero W. The camera controllers 91 are coupled to a hub controller 100, which may be a Raspberry Pi 4, or any other suitable computing device. The hub controller 100 communicates with each of the camera controllers 91 using any suitable wired or wireless communication interface.

The hub controller 100 is configured to command the cameras 44 to capture images, store captured images, process images, tag images, and the like. The images may be stored in any suitable file format, such as JPEG, RAW, etc. The hub controller 100 is also coupled to a hardware controller 102 using any suitable interface 100a, such as USB. The hardware controller 102 may be any suitable computing device, such as an Arduino Uno and is configured to control movement of the actuators 16. In particular, the hub controller 100 is configured to output a movement command based on a desired distance movement and the hardware controller 102 is configured to translate the movement command into a number of discrete steps for moving the actuators 16 to achieve the desired movement command. The hub controller 100 is also coupled to one or more relays 112, which are configured to toggle the first illumination assembly 50 and the second illumination assembly 80 individually as well as shut off power to the entire imaging device 10 in the event of an emergency via a kill switch 113.

The hub controller 100 is also coupled to a lower limit switch 15 and an upper limit switch 17 (FIG. 2) engageable by the elevator platform 20 upon reaching lower and upper limits, respectively. In addition, the hub controller 100 is further coupled to a temperature and/or humidity sensor 117. Sensor data from the sensor 117 is provided to the hub controller 100. In the event humidity or temperature is outside operating limits, the hub controller 100 shuts down the imaging device 10, thereby protecting the imaging device 10 and the samples.

The sensor 117 may be used in conjunction with the fan 11 to control the temperature of the imaging device 10. In embodiments, the hub controller 100 may control the fan 11 (e.g., turning the fan 11 on or off, adjusting the speed, etc.) based on the temperature and/or humidity measurement data from the sensor 117. This is particularly useful when using the imaging device 10 with temperature sensitive samples and/or environment. In particular, the imaging device 10 may be used in temperature and/or humidity-controlled $CO_2$ incubators. If the sensor 117 senses that temperature is excessive, then the hub controller 100 can shut down the imaging device 10 to prevent the incubator for overheating and preserving the cell culture samples "S" or increase the circulation of the fan 11.

The imaging process includes placing the cell culture plate 70 on the alignment platform 60. This may also include adjusting the position of the cell culture plate 70 on the alignment platform 60 along the x and y axes to align the wells 72 with the imaging units 40. The hub controller 100 may then take images of the samples "S" held by the alignment platform 60 to confirm that the samples "S" are adequately illuminated and are in focus. The hub controller 100 may set light color and intensity of the first illumination assembly 50 and the second illumination assembly 80. The hub controller 100 also adjusts the vertical position of the elevator platform 20 to achieve desired focus of the images. Once these settings are finalized, the hub controller 100 may be programmed to set the duration of the longitudinal study, which may be from about 1 hour to about 30 weeks. The hub controller 100 also configures the frequency of the images being taken during the study period. After each set of pictures, the imaging unit returns to the lowest ("park") position, which is determined by activation of the lower limit switch 15 by the elevator platform 20.

Figure 5A:
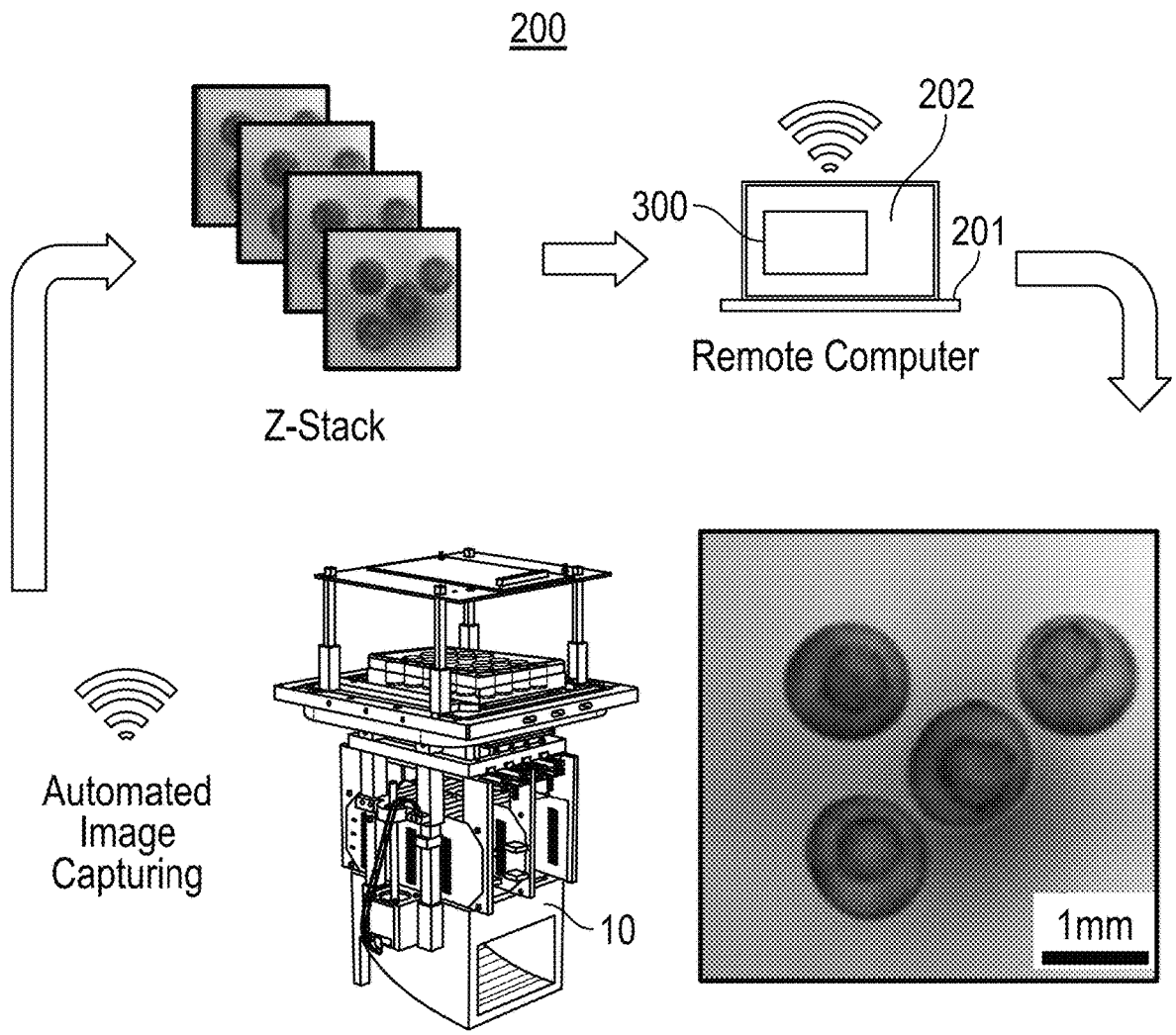
FIG. 5A is a schematic diagram of an imaging system including the imaging device and a computer according to one embodiment of the present disclosure.

With reference to FIG. 5A, an imaging system 200 is shown, which includes the imaging device 10 in communication with a computer 201, which may be a laptop, a desktop, a server, or a virtualized computer, in communication with the imaging device 10. The computer 201 may be coupled to the imaging device 10 using a wired interface, such as USB, or any communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

As noted above, the hub controller 100 may include any suitable wireless or wired interface for connecting to the computer 201. The images may then be transferred to the computer 201, where the images can be viewed and/or processed with minimal intervention as shown in an exemplary image of FIG. 12. The computer 201 may also include a display 202 allowing for viewing of the images. In addition, the computer 201 may be used to input experiment and operating parameters for the imaging device 10 via the hub controller 100.

Figure 5B:
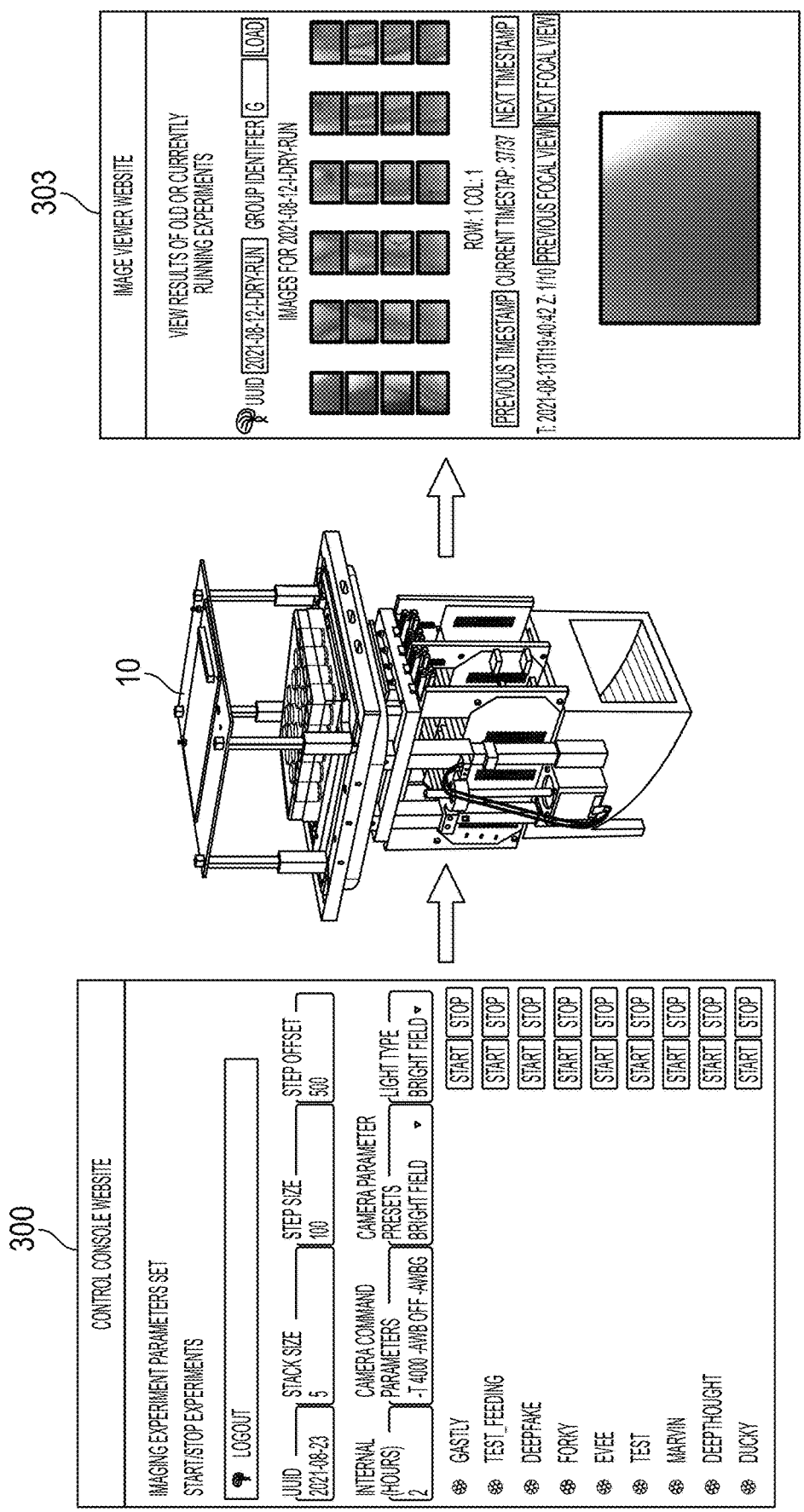
FIG. 5B is a schematic diagram of a workflow of the imaging system and the computer of FIG. 5A according to one embodiment of the present disclosure.

With reference to FIG. 5B, the computer 201 may execute a control console application 300 for controlling the imaging device 10. In embodiments, the control console 300 may be embodied as a web page and the computer 201 may be configured to execute a web browser or any other application for accessing the web page. As used herein, the term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, a personal computer, or a server system. The computer 201 is also configured to execute an image viewer 303, which allows for viewing of the images produces by the imaging device 10. The image viewer 303 may also be embodied in a web browser or a separate software application.

Figure 6A:
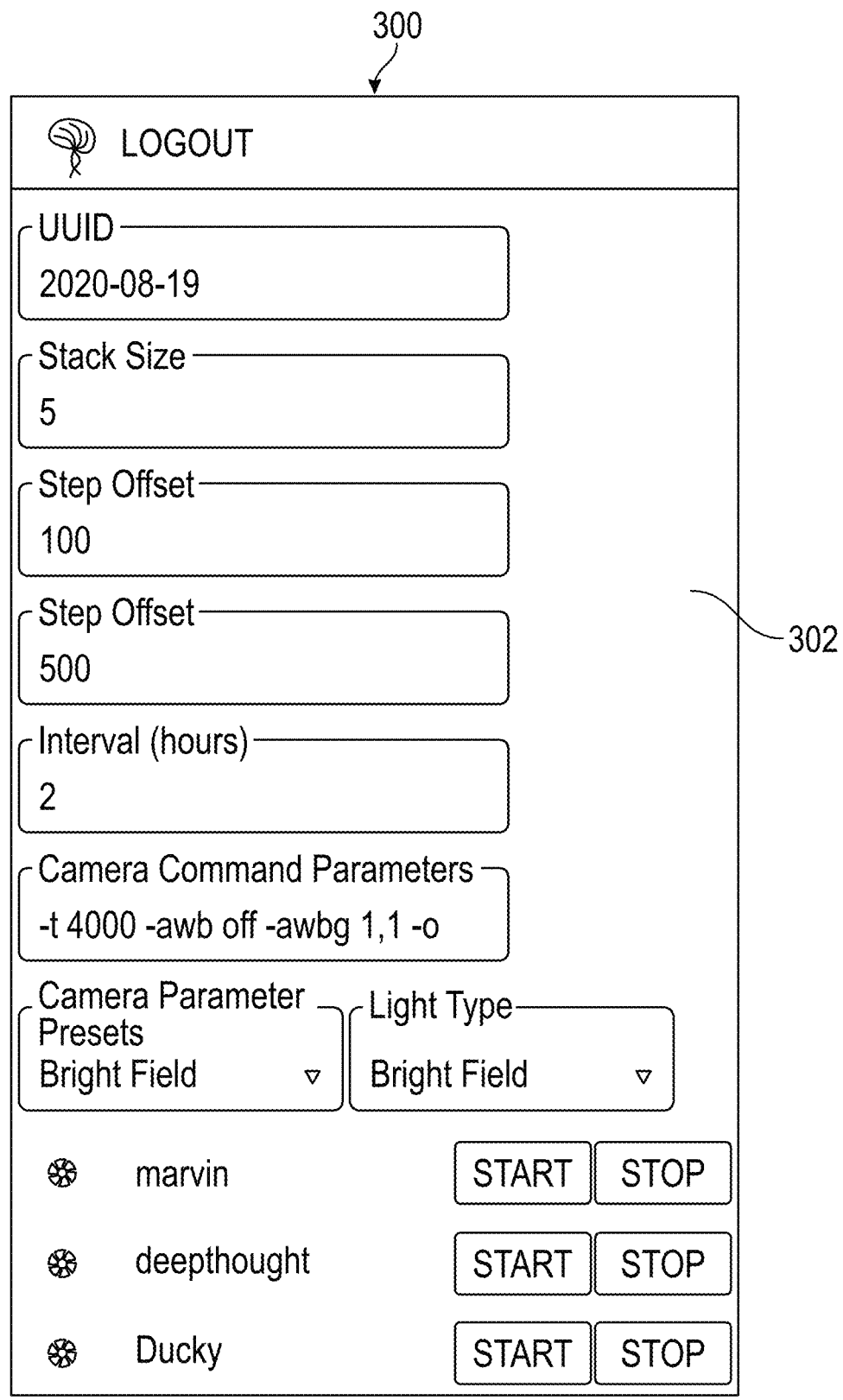
FIG. 6A is an image of a graphical user interface of a control console of the computer of FIG. 5A according to one embodiment of the present disclosure.

With reference to FIG. 6A, the control console 300 includes a graphical user interface (GUI) 302 having a plurality of parameters which may be entered by a user. The GUI 302 may have a plurality of elements, such as text fields, drop down menus, slides, buttons, bullet selectors, etc. The GUI 302 allows the user to enter various imaging experiment parameters including, but not limited to, name or identifier of the experiment, stack size—which defines number of focal planes at which images are taken, step size—which defines the distance between each focal plane, step offset—which defines the distance for the first image of the stack, interval—time between images, duration of the imaging experiment, etc. The GUI 302 also allows for entering text-based camera command parameters, such as white balance and exposure settings. In addition, drop down menus may be used to adjust presets for lighting and other corresponding camera presets.

Figure 7:
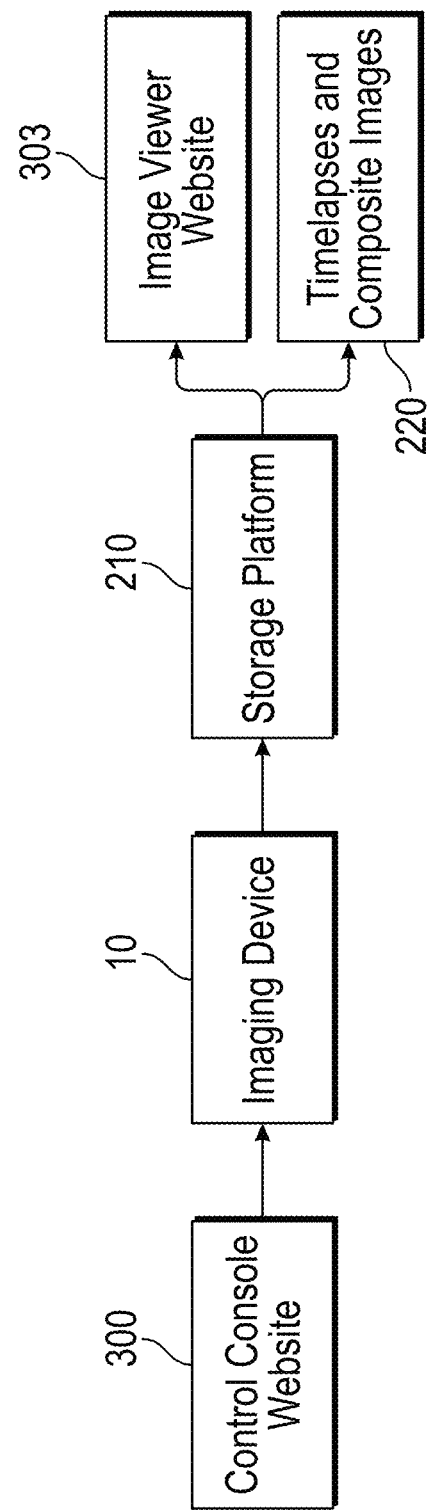
FIG. 7 is a flow chart of operating the imaging system of FIG. 5A according to one embodiment of the present disclosure.
Figure 8:
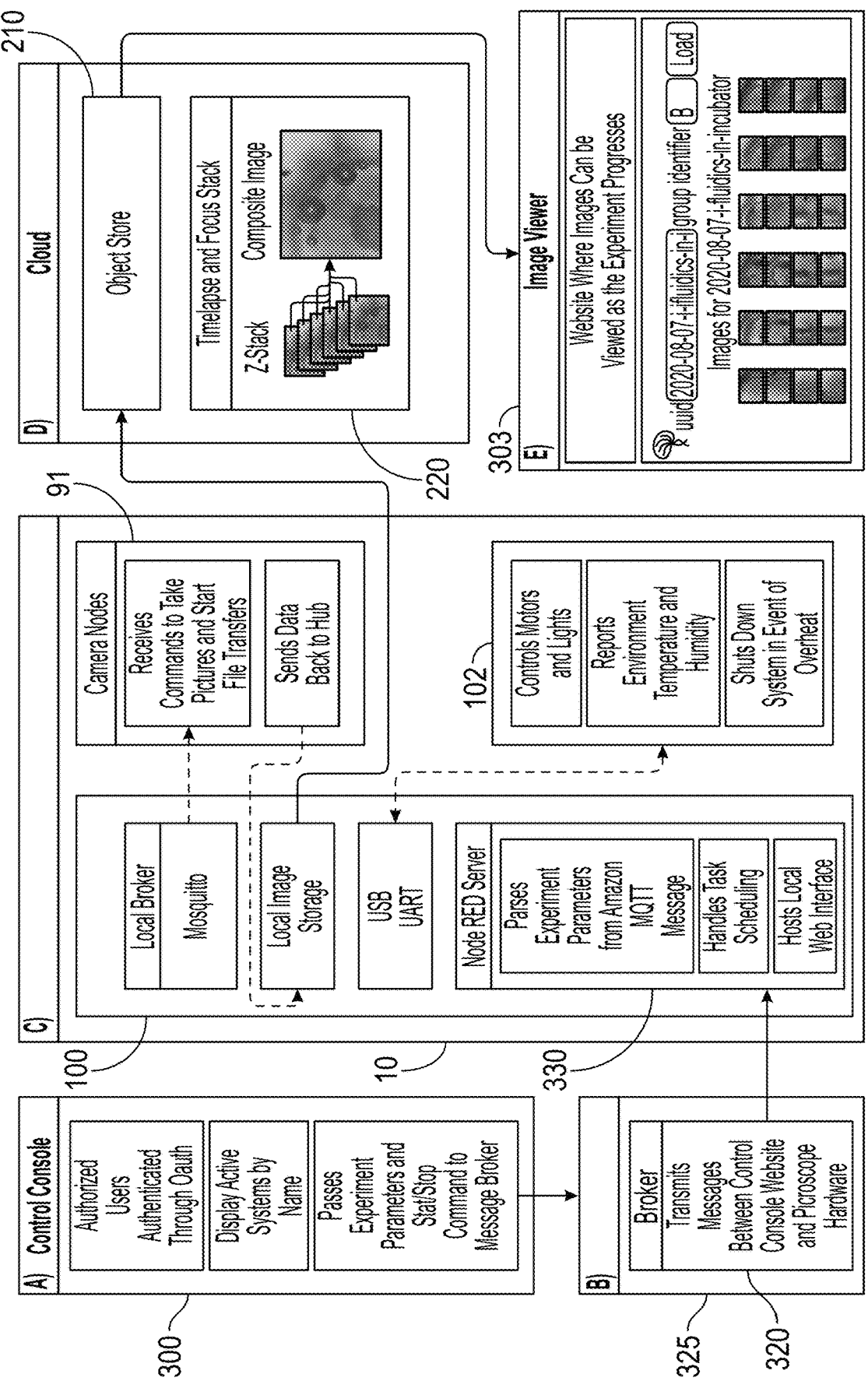
FIG. 8 is a schematic diagram of the imaging system illustrating data flow according to one embodiment of the present disclosure.

With reference to FIG. 7, a flow chart of a method for operating the imaging device 10 initially involves the user setting up experiment parameters through the control console 300, and in particular, the GUI 302. Experiment setup includes inputting parameters, such as experiment identifier, number of images in a stack, distance between imaging layers (i.e., focal planes), initial offset distance, light type, duration of experiment, time between each of the imaging sequences, the first illumination assembly 50 or the second illumination assembly 80, camera control parameters, etc. The imaging sequence may include imaging at a single focal plane or imaging at a plurality of focal planes to obtain a z-stack of images. FIG. 8 illustrates the flow of data between the computer 201, the imaging device 10 and other components of FIG. 7.

A publish-subscribe network protocol, such as Message Queuing Telemetry Transport (MQTT), or any other suitable protocol may be used to transmit parameters. The commands may be organized by time steps and each time step data point may include one z-stack per active imaging unit 40. A publish-subscribe network protocol may be configured to transfer commands and/or messages published on any topic to all subscribers, i.e., imaging devices 10, of that topic using a broker 320, which may be executed on a cloud server 325, such as Amazon IoT. Each of the imaging devices 10 is identified using a unique identifier and includes its own broker 330 executed by the hub controller 100. Thus, a plurality of imaging devices 10 may be controlled by a single computer 201. The control console 300 may provide a list of imaging device 10 and corresponding status, i.e., active or inactive. The list may be displayed on the GUI 302 and the user may select which of the imaging device 10 are to be controlled for a specific experiment. When a command is sent from the control console 300, the command is published with the topic being the specific identifier of the imaging device 10 being controlled.

The targeted imaging device 10 receives the command along with desired experiment parameters, which may also be adjusted in real-time from the control console 300. Upon receiving the command and parameters, the imaging device 10 generates a manifest file 310 (FIG. 10) storing the parameters. The manifest file 310 also maintains a log and is updated every time a new data point is captured by any of the imaging units 40.

The imaging device 10, and in particular, the hub controller 100 is configured to execute a local broker 330 that is configured to communicate with broker 320. The local broker 330 of the imaging device 10 passes commands through the hub controller 100 to each of the camera controllers 91 as well as to the hardware controller 102 to move the elevator platform 20 thereby adjusting the distance between the imaging assembly 30 and the cell culture plate 70. The commands to the camera controllers 91 may include activating any number of the imaging units 40, e.g., one or more. The commands may also include disabling certain imaging units 40, such as those disposed imaging units 40 over unused wells 72 of the cell culture plate 70.

With reference to FIG. 4, the hub controller 100 receives experiment parameters from the computer 201 via the control console 300. The image capture process includes the hub controller 100 turning on the first illumination assembly 50 or the second illumination assembly 80 based on the parameter settings. During image capture, including z-stack capture, the imaging assembly 30 is moved to the starting position as defined by the step offset parameter. The hub controller 100 also sends command(s) to the individual camera controllers 91, which operate corresponding imaging units 40. The commands include input parameters entered through the control console 300. The images captured by the imaging units 40 are stored in each of the corresponding camera controllers 91. Once all of the imaging units 40 have finished capturing images, the elevator platform 20 is moved, i.e., upwards, to the next level based on the step size parameter, at which point the next layer of the z-stack is captured. This process is repeated until each layer of the z-stack is obtained. If only a single image is to be taken, the imaging assembly 30 may be moved to any desired position.

After each imaging unit 40 takes a picture, the corresponding camera controller 91 transmits a message to the hub controller 100 with a camera identifier. The hub controller 100 updates the log of the manifest file 310. At the conclusion of the image capture, the elevator platform 20 with the imaging assembly 30 is moved, i.e., lowered, to a starting position, which is sensed by the lower limit switch 15. Once the starting position is reached, the hub controller 100 sends a command to each of the camera controllers 91 to initialize file transfer to the hub controller 100.

Figure 9:
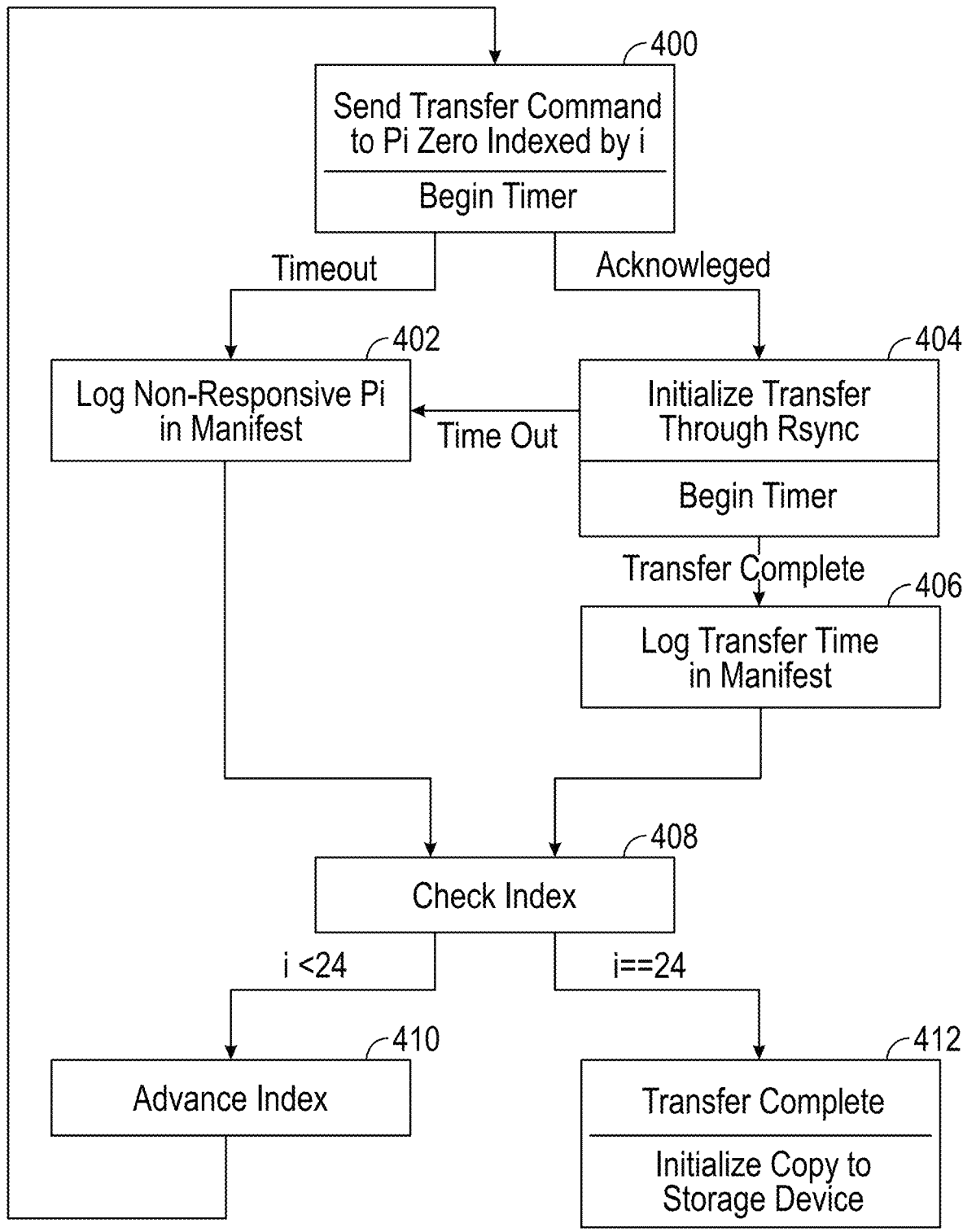
FIG. 9 is a flow chart of a method for image transfer between a hub controller and imaging units of the imaging device according to one embodiment of the present disclosure.

Images may be transferred in a parallel manner using any suitable file synchronization utility, such as rsync. The imaging device 10 may also utilize an image transfer utility, which is shown as a method in FIG. 9. The method is embodied as a software application executed by the hub controller 100. The image transfer utility incorporates a queueing protocol, which involves sequentially querying each of the camera controllers 91 in a sequential manner. The hub controller 100 sends a command requesting image transfer to, i.e., queries, individually each of the camera controllers 91 in a predetermined sequence, i.e., an index of the imaging units—lowest to highest identifier of the imaging unit 40. The hub controller 100 then proceeds to send the query the next camera controller 91 after the image transfer is complete. The method includes various acknowledgement checks and timers so that the queue is not disrupted in case of unresponsive camera controllers 91.

Initially, at step 400, the hub controller 100 sends a transfer command requesting image transfer to one of the camera controllers 91, which is selected based on the index of camera controllers 91. The hub controller 100 also begins a first timer during which the hub controller 100 is waiting for an acknowledgement from the camera controller 91 being queried. If the first timer expires before an acknowledgement is received, the hub controller 91 at step 402 logs the camera controller 91 as non-responsive in the manifest file 310. If the request is acknowledged, at step 404, the camera controller 91 initializes file transfer using any suitable file synchronization protocol and initializes a second timer. If the second timer expires before the file transfer is complete, the hub controller 100 once again logs the camera controller 91 as non-responsive in the manifest file 310. If the file transfer is complete before expiration of the second timer, the camera controller 91 transmits confirmation of completion to the hub controller 100, which at step 406 logs the file transfer confirmation and the transfer time in the manifest file 310.

At step 408, the hub controller 100 checks the index to obtain the identifier of the next camera controller 91. The hub controller 100 verifies if the current index less than or equal to the maximum index value, which corresponds to the total number of imaging units 40, e.g., 24. If the index value is less than the maximum index value, the index is advanced at step 410 and the hub controller 100 repeats the process starting at step 400. If the index value is the same as the maximum index value, then the hub controller determines that each of the camera controllers 91 has been queried and at step 412 initializes file transfer of all the images to a storage device 210 (FIGS. 7 and 8), which may be a remote server, a cloud storage service, or any other storage device.

With reference to FIGS. 7 and 8, the storage device 210 may transmit images to an image processing platform 220, which may be a virtualized computer, a containerized application (e.g., Docker), a cloud server or service, or any other computing platform. In embodiments, the storage device 210 may also include image processing capabilities. The hub controller 100 transfers all of the image files and the manifest file 310 to the storage device 210. The storage platform 210 is configured to parse the manifest file 310 match each of the images to the entries in the manifest file 310 and generate links and/or web pages including the images that are viewable by the control console 300, such that the collected images on the storage platform 210 are accessible by the computer 201.

Figure 6B:
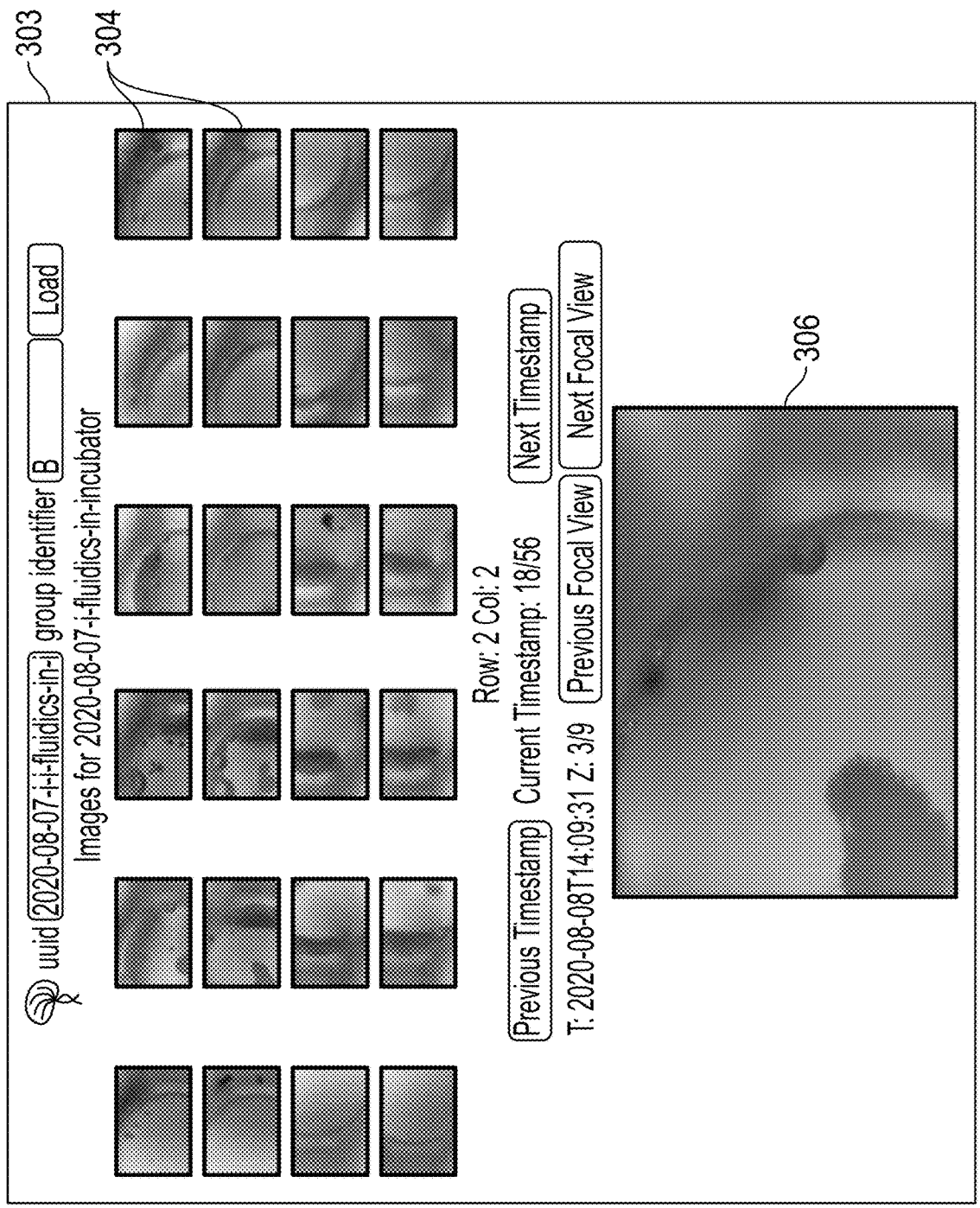
FIG. 6B is an image of an image viewer of the computer of FIG. 5A according to one embodiment of the present disclosure.

With reference to FIG. 6B, the computer 201 is also configured to execute the image viewer 303, which allows for viewing of the images produces by the imaging device 10. The image viewer 303 may also be embodied in a web browser or a separate software application. Each of the wells 72 is represented by a corresponding image 304, each of which was captured by an individual camera 44. Thus, the control console 300 provides users with independent virtual microscopes with near real time views of the samples "S" held within each of the well wells 72 at different focal planes. Additionally, an enlarged viewing area 306 may be presented by selecting any of the images 304. The images may be displayed on a web page and be viewable by a browser.

Figure 10:
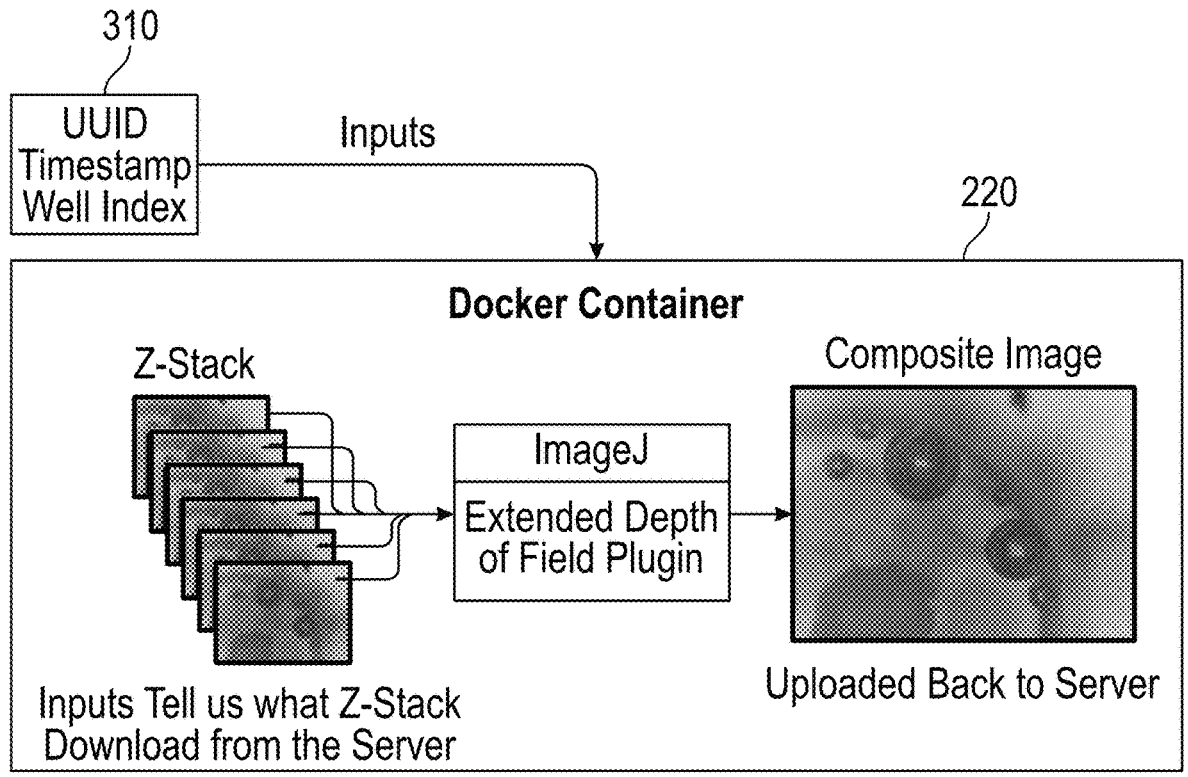
FIG. 10 is a schematic diagram of an image processing method according to one embodiment of the present disclosure.

With reference to FIG. 10, the images on the storage platform 210 may be further processed on the image processing platform 220 to generate timelapse videos or focal plane stacked composite images using information, including time stamps of the images, from the manifest file 310 to match related images. The output of the image processing platform 220 may be provided to the storage platform 210 and/or the image viewer 303. The image processing platform 220 receives the manifest file 310, which provides a list of images, i.e., file names, and proceeds to download and process the images listed in the manifest file 310. As used herein, a timelapse video includes a plurality of images taken at the same focal plane of the same sample over a period of time, each frame of the video being a discrete image captured by an individual camera 44. A focal plane stacked composite (i.e., EDoF) image combines a plurality of images of the same sample taken at different focal planes at the same time (discounting the time taken to move between focal planes) as shown in FIG. 10. The timelapse videos and the EDoF composite images generated by the image processing platform 220 may be initially uploaded to the storage platform 210. The user may then access the generated timelapse videos and the EDoF composite images for viewing using the image viewer 303.

The computing devices (e.g., camera controllers 91, hub controller 100, computer 201, storage device 210, the image processing platform 220, etc.) according to the present disclosure may be a virtualized computer, containerized application (e.g., Docker), or any other computing platform having a processor operably connected to a memory, which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

The following Examples illustrate embodiments of the present disclosure. These Examples are intended to be illustrative only and are not intended to limit the scope of the present disclosure.

Example 1

This Example describes in-incubator imaging of human embryonic stem cells and brain organoids using the imaging device according to the present disclosure.

While many biological systems including zebrafish, planaria and frogs develop at room temperature and atmospheric gas concentrations, mammalian models require special conditions requiring an incubator enclosure. Mammalian models include 2D monolayer cell cultures, as well as 3D organoid models of development and organogenesis. They have been used to assess molecular features and effects of drugs for a variety of phenotypes including cell proliferation, morphology, and activity, among others.

Deploying electronics and 3D printed materials inside tissue culture incubators, which have increased humidity and temperature, presents some unique challenges. Increased temperature and humidity conditions can cause electronics to fail and cause certain plastics to off-gas toxins.

Plastics can also be prone to deformation in these conditions. A common solution for protecting electronics and preventing off-gassing is to use inert protective coatings e.g., Parylene C. This requires expensive clean room equipment.

The imaging device according to the present disclosure is formed from 3D printed components from PLA, a non-toxic and biodegradable material. In order to prevent deformation, structural components were printed using 100% infill and reinforced vulnerable elements with aluminum MakerBeam profiles. All electronic components were coated with Corona Super Dope Coating from MG Chemicals to protect the electronics from the conditions, e.g., heat and humidity, of an incubator.

Figure 11:
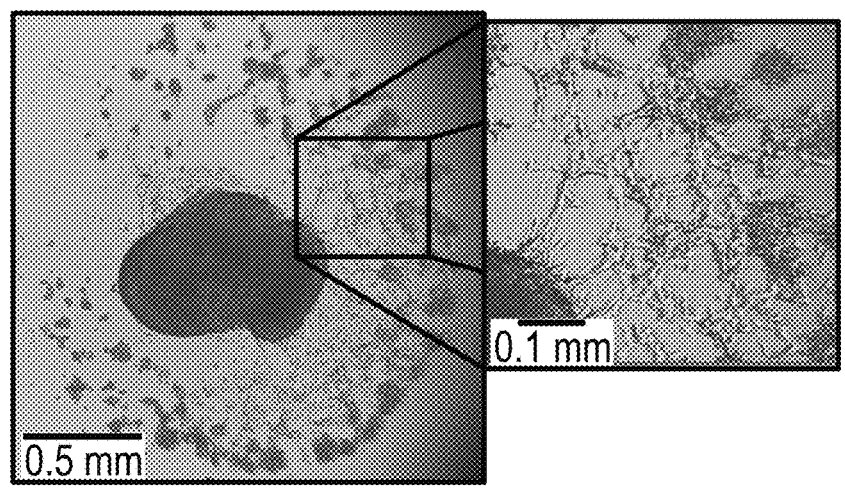
FIG. 11 shows images of a neuronal culture with outgrowths captured using the image device of FIG. 1.

The functionality of the imaging device was tested inside a standard tissue culture incubator, i.e., by imaging 2D-monolayers of human embryonic stem cells (hESCs). Neuron cell cultures were monitored over the course of a 3-week period inside a temperature and humidity-controlled CO2 incubator. A sample image from that experiment is shown in FIG. 11. Thus, it was demonstrated that the imaging device according to the present disclosure is feasible for longitudinal imaging of mammalian cell and organoid models.

All hESC experiments used the H9 cell line (WiCell). hESCs were grown on vitronectin (Thermo Fisher Scientific, A14700) coated plates and cultured using StemFlex Medium (Thermo Fisher Scientific, A3349401). Passages were performed incubating the cells in 0.5 mM EDTA (Thermo Fisher Scientific, 15575020), in DPBS for 5 minutes.)

To generate cortical organoids, hESCs were first dissociated into single cells and re-aggregated them in Aggrewell 800 24-well plates (STEMcell Technologies) at a density of about 3,000,000 cells per well with 2 mL of Aggrewell Medium (STEMcell Technologies) supplemented with Rho Kinase Inhibitor (Y-27632, 10 Tocris, 1254) (Day 0). The following day (Day 1), the aggregates were supplemented with WNT inhibitor (IWR1-ε, 3 Cayman Chemical, 13659, Days 1-10) and TGF-βinhibitor (SB431542, Tocris, 1614, 5 days 0-10). On Day 2, aggregates were transferred by pipetting out of the Aggrewell plate with a wide bore P1000 pipette tips onto a 37 μm filter and then transferred to ultra-low adhesion 6-well plates. Media was changed on Days 4, 8 and 10, by replacing 2 mL of conditioned media with fresh media. On Day 11 the medium was changed to Neuronal Differentiation Medium containing Eagle Medium: Nutrient Mixture F-12 with GlutaMAX supplement (DMEM/F12, Thermo Fisher Scientific, 10565018), 1X N-2 Supplement (Thermo Fisher Scientific, 17502048), 1X Chemically Defined Lipid Concentrate (Thermo Fisher Scientific, 11905031) and 100 U/mL Penicillin/Streptomycin supplemented with 0.1% recombinant human Fetal Growth Factor b (Alamone F-170) and 0.1% recombinant human Epidermal Growth Factor (R&D systems 236-EG). On Day 12, the organoids were transferred in 90 μL media to a custom glass-PDMS microfluidic chip for imaging/feeding containing 50 μL Matrigel hESC Qualif Matrix (BD 354277) bringing the total volume in the well to 120 μL. Partially embedding the organoid in Matrigel in this way led to 2D outgrowths on the surface of the Matrigel. Feeding occurred automatically every hour replacing 30 μL Neuronal Differentiation Medium.

Example 2

This Example describes imaging of *Xenopus tropicalis* (frog) embryos using the imaging device according to the present disclosure.

Longitudinal live imaging capabilities of the imaging device according to the present disclosure were examined by imaging the development of frog embryos from the onset of gastrulation through organogenesis. The fertilization and development of *Xenopus* occurs entirely externally, which allows scientists to easily observe and manipulate the process. For decades, *Xenopus* have been heavily used in biology studies to model a variety of developmental processes and early onset of diseases, particularly those of the nervous system. While several species of *Xenopus* are used in different laboratories around the world, *Xenopus tropicalis* is one of the preferred species due to its diploid genomic composition and fast sexual maturation. Normal development and optimal husbandry of *Xenopus tropicalis* occurs at about 25° C. to about 27° C., closely approximating standard room temperature, which eliminates the need of special environmental control for most experiments.

Given these convenient experimental advantages and their large size, *Xenopus* embryos have been used extensively to understand the development of the vertebrate body plan, with particular success in elaborating the complex cellular rearrangements that occur during gastrulation and neural tube closure. These experiments rely on longitudinal imaging of developing embryos, often at single-embryo scale with dyes, fluorescent molecules, and computational tracking of single cells. These studies have elucidated key cellular mechanical properties and interactions critical to vertebrate development, often replayed and co-opted during tumorigenesis. There exists an opportunity to scale these experiments to have a higher throughput with the imaging device according to the present disclosure, as one could image hundreds of developing embryos simultaneously, rather than having to move the objective from embryo-to-embryo during development or repeating the experiment many times.

Figure 12:
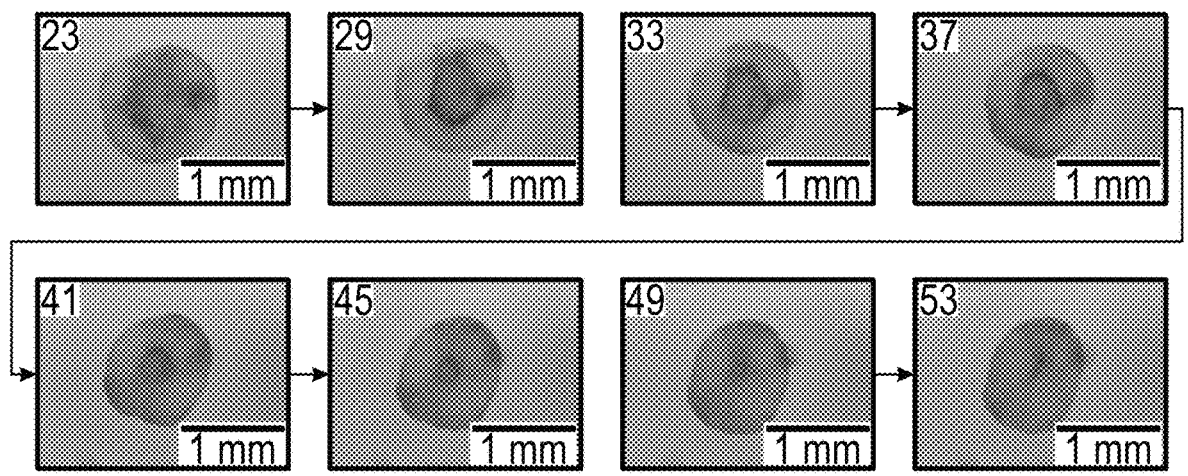
FIG. 12 shows images of frog embryos captured using the image device of FIG. 1.

Development of frog embryos into larvae was monitored all stages of development were imaged as the embryo grew into a moving larva. Many experiments have been done investigating factors that affect this development, using the imaging device of the present disclosure allowed high frequency image capture of these developmental stages without need for user interference. FIG. 12 shows cell division in the early part of the experiment showing the changes that occur in the first 3 hours of development. In particular, FIG. 12 shows blastopore closure, an important part of gastrulation and a phase of interest in several studies. This example demonstrated that the imaging device can be used for longitudinal sequential imaging and tracking of biological systems.

Example 3

This Example describes imaging of zebrafish embryos using the imaging device according to the present disclosure.

Zebrafish Fertilized zebrafish eggs were purchased from Carolina Biological Supply Company (Catalog #155591) and maintained in media containing 15 mM sodium chloride (Sigma-Aldrich, S9888), 0.5 mM potassium chloride (Sigma-Aldrich, P3911), 1 mM calcium chloride dihydrate (Sigma-Aldrich, 223506), 1 mM magnesium sulfate heptahydrate (Sigma-Aldrich, 1058822500), 150 μM potassium phosphate monobasic (Sigma-Aldrich, P5655), 50 μM sodium phosphate dibasic heptahydrate (Sigma-Aldrich, S9390), 0.7 mM sodium bicarbonate (Sigma-Aldrich, S5761) and 0.1% methylene blue (Sigma-Aldrich, M9140).

Figure 13:
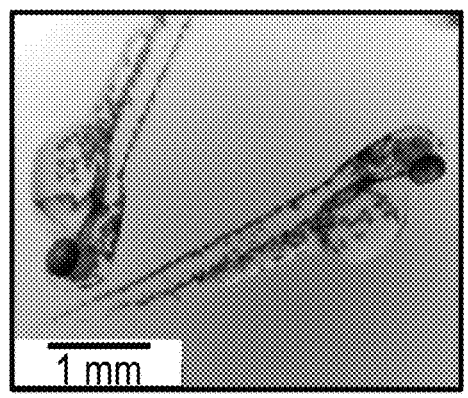
FIG. 13 is an image of zebrafish embryos captured using the image device of FIG. 1.

In this example, the imaging device was used to measure survival and behavioral changes of zebrafish under the influence of varying concentrations of caffeine. During the setup phase of this experiment, video showing fluid circulation inside a live zebrafish was captured. This demonstrated the video capture capability which can be used to observe higher frequency dynamics. FIG. 13 shows a still image from the video.

It will be appreciated that of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims. Unless specifically recited in a claim, steps or components according to claims should not be implied or imported from the specification or any other claims as to any particular order, number, position, size, shape, angle, or material.

What is claimed is:

1. An imaging system comprising:
    an imaging device operable inside an incubator, the imaging device including:
        a holder configured to hold a cell culture plate having a plurality of wells;
        an imaging assembly including a plurality of imaging units, each of which is configured to image one well of the plurality of wells;
        an actuator for moving the imaging assembly relative to the cell culture plate such that each of the imaging units is configured to capture an image at each focal plane of a plurality of focal planes;
        a plurality of camera controllers each of which is configured to control an imaging unit of the plurality of imaging units; and
        a hub controller configured to execute an image transfer utility incorporating a queuing protocol for sequentially querying each of the plurality of camera controllers to receive a plurality of images;
    a storage platform in communication with the imaging device configured to receive the plurality of images from the hub controller; and
    a computer disposed outside the incubator and in communication with the imaging device and the storage platform, the computer configured to control the imaging device and to display at least one image of the plurality of images.

2. The imaging system according to claim 1, further comprising:
    an image processing platform configured to at least one of generate a time lapse video from the plurality of images or an extended depth of field composite image from the plurality of images.

3. The imaging system according to claim 1, wherein each of the imaging units is configured to capture a plurality of images of a corresponding well over a period of time.

4. The imaging system according to claim 1, wherein the imaging assembly is movable relative to the cell culture plate such that each of the imaging units is configured to capture an image at each focal plane of the plurality of focal planes.

5. The imaging system according to claim 1, wherein the computer further includes a control console configured to receive at least one parameter as user input and to transmit the at least one parameter to the imaging device.

6. The imaging system according to claim 1, wherein the imaging device further includes a hub controller and a plurality of camera controllers, each of which is coupled to one imaging unit of the plurality of imaging units.

7. The imaging system according to claim 6, wherein the hub controller is further configured to query each of the camera controllers in a sequential manner.

8. The imaging system according to claim 7, wherein each of the camera controllers is configured to transmit at least one image as a response to a query from the hub controller.

9. The imaging system according to claim 8, wherein the hub controller is further configured to check whether the response from each of the camera controllers has timed out.

10. A method for imaging a cell culture plate using an imaging device, the method comprising:
    receiving at least one parameter at an imaging device operable inside an incubator, the imaging device including:
        a holder configured to hold a cell culture plate including a plurality of wells;
        an imaging assembly including a plurality of imaging units, each of which is configured to image one well of the plurality of wells;
        an actuator for moving the imaging assembly relative to the holder along a vertical axis transverse to a plane defined by the holder; and
        a plurality of camera controllers each of which is configured to control an imaging unit of the plurality of imaging units;
    operating the imaging device based on the at least one parameter to capture at least one image of at least one well;
    executing an image transfer utility incorporating a queuing protocol for sequentially querying each of the plurality of camera controllers to receive a plurality of images; and
    transmitting at least one image of the plurality of images to a storage platform.

11. The method according to claim 10, wherein the at least one parameter is a number of focal planes.

12. The method according to claim 11, further comprising:
    moving the imaging assembly relative to the holder along the vertical axis transverse to the plane defined by the holder and stopping the imaging assembly at each of the focal planes.

13. The method according to claim 12, further comprising:
    operating the imaging assembly to capture an image at each of the focal planes.

14. The method according to claim 13, further comprising:
    generating an extended depth of field composite image from the images taken at each of the focal planes.

15. The method according to claim 10, wherein the at least one parameter is a number of imaging sequences over a time period.

16. The method according to claim 15, further comprising:
    operating the imaging assembly for the number of imaging sequences over the time period.

17. The method according to claim 16, further comprising:
    generating a time lapse video from images taken during the imaging sequence.

18. The method according to claim 10, further comprising:
 inputting the at least one parameter at a control console including a graphical user interface.

19. The method according to claim 18, further comprising:
 displaying the at least one image on an image viewer of the control console.

\* \* \* \* \*